United States Patent

Stetter et al.

[11] Patent Number: 5,939,441
[45] Date of Patent: Aug. 17, 1999

[54] SUBSTITUTED PYRIDYLPYRAZOLES

[75] Inventors: Jörg Stetter, Wuppertal; Bernd Alig, Königswinter; Albrecht Marhold; Norbert Mencke, both of Leverkusen; Klaus Mrusek, Bergisch Gladbach; Andreas Turberg, Erkrath, all of Germany

[73] Assignee: Bayer Aktiengesellschaft, Leverkusen, Germany

[21] Appl. No.: 08/423,190

[22] Filed: Apr. 18, 1995

[30] Foreign Application Priority Data

Apr. 25, 1994 [DE] Germany .................................. 4414333

[51] Int. Cl.$^6$ ........................ A61K 31/44; C07D 401/04
[52] U.S. Cl. ............................ 514/341; 546/276.1
[58] Field of Search ..................... 546/279, 276.1; 514/341

[56] References Cited

U.S. PATENT DOCUMENTS

| 4,772,312 | 9/1988 | Schallner et al. ................ | 546/279 |
| 4,945,165 | 7/1990 | Jensen-Korte et al. .............. | 546/279 |

FOREIGN PATENT DOCUMENTS

| 0201852 | 11/1986 | European Pat. Off. . |
| 0207285 | 1/1987 | European Pat. Off. . |
| 0235628 | 9/1987 | European Pat. Off. . |
| 0500209 | 8/1992 | European Pat. Off. . |

*Primary Examiner*—Jane Fan
*Attorney, Agent, or Firm*—Sprung Horn Kramer & Woods

[57] ABSTRACT

The invention relates to new substituted pyridylpyrazoles of the general formula (I)

in which
  n represents the number 0, 1 or 2,
to a plurality of processes for their preparation, to their use as pesticides and for combating arthropods, and to a new intermediate.

5 Claims, No Drawings

SUBSTITUTED PYRIDYLPYRAZOLES

The invention relates to new substituted pyridylpyrazoles, to a plurality of processes for their preparation, to their use as pesticides, and for combating arthropods, and to a new intermediate.

It is already known that certain substituted 1-arylpyrazoles such as, for example, 5-amino-1-[2,6-dichloro-4-(trifluoromethyl)-phenyl]-3-cyano-4-[(trifluoromethyl)-sulfinyl]-1H-pyrazole, have a good activity against pests (cf., for example, EP-A 295 117 and EP-A 352 944).

Furthermore, a large number of substituted 1-arylpyrazoles which can be employed for combating pests have been described (cf., for example, EP-A 201 852, EP-A 418 016).

In addition, substituted 1-arylpyrazoles also act as intermediates for the preparation of pesticides (cf., for example, EP-A 301 338, EP-A 301 339, EP-A 374 061, EP-A 260 521).

However, the level or duration of activity of the prior art compounds is not entirely satisfactory in all fields of application, in particular in the case of certain insects or when low concentrations are applied.

New substituted pyridylpyrazoles of the general formula (I)

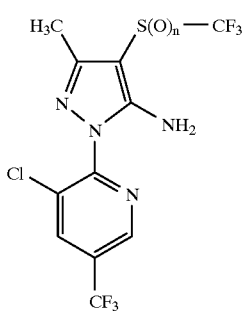

in which
n represents the number 0, 1 or 2
have now been found.

Furthermore, it has been found that the new substituted pyridylpyrazoles of the general formula (I) are obtained by one of the processes described hereinbelow:

a) 5-Amino-3-methyl-4-trifluoromethylthio-[(3-chloro-5-trifluoromethyl)-2-pyridyl]-pyrazole, of the formula (Ia), (Ia)

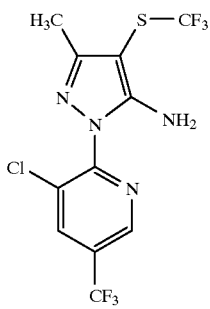

is obtained by a process which comprises reacting 5-amino-3-methyl-[(3-chloro-5-trifluoromethyl)-2-pyridyl]-pyrazole of the formula (II)

(II)

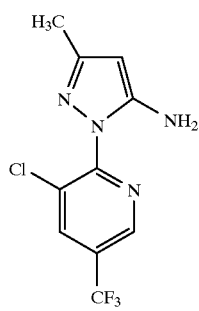

with trifluoromethylsulfenyl halides of the formula (III)

$$CF_3\text{—}S\text{—}Hal \quad (III)$$

in which
Hal represents halogen, in particular chlorine or bromine, if appropriate in the presence of a diluent and if appropriate in the presence of a reaction auxiliary.

b) Substituted pyridylpyrazoles of the formula (Ib)

(Ib)

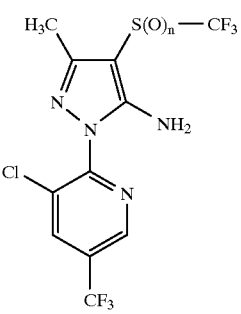

in which
n represents the number 1 or 2
are obtained by a process which comprises oxidizing 5-amino-3-methyl-4-trifluoromethylthio-[(3-chloro-5-trifluoromethyl)-2-pyridyl]-pyrazole of the formula (Ia)

(Ia)

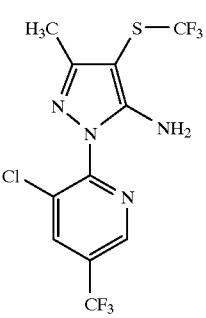

with oxidants in the presence of a diluent and if appropriate in the presence of a catalyst.

Finally, it has been found that the new substituted pyridylpyrazoles of the formula (I) have a very potent activity against pests, in particular a very potent insecticidal and acaricidal activity.

Surprisingly, the pyridylpyrazoles of the formula (I) according to the invention have a considerably better activity against animal pests than the prior-art compounds of a similar constitution.

5-Amino-3-methyl-[(3-chloro-5-trifluoromethyl)-2-pyridyl]-pyrazole of the formula (II), which is required for carrying out process (a) according to the invention, is new and part of the invention. It can be obtained by generally known processes in an analogous manner by a process which comprises heating 3-aminocrotonitrile of the formula (IV)

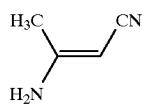

(IV)

and 3-chloro-5-(trifluoromethyl)-2-pyridyl-hydrazine of the formula (V)

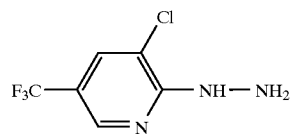

(V)

at temperatures between 20° C. and 100° C., if appropriate in the presence of a diluent such as, for example, ethanol or glacial acetic acid, and if appropriate in the presence of a reaction auxiliary such as, for example, sulfuric acid (cf. EP-A 201 852 and Preparation Example).

The compounds of the formulae (IV) and (V) are generally known compounds of organic chemistry.

The trifluoromethylsulfenyl halides of the formula (III) which are furthermore required for carrying out process (a) according to the invention are also generally known compounds of organic chemistry.

5-Amino-3-methyl-4-trifluoromethylthio-[(3-chloro-5-trifluoromethyl)-2-pyridyl]-pyrazole of the formula (Ia), which is required as starting substance for carrying out process (b) according to the invention, is new and part of the invention. It can be obtained by process (a).

Suitable diluents for carrying out process (a) according to the invention are inert organic solvents. These include, in particular, aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform, carbon tetrachloride, ethers such as diethyl ether, dioxane, tetrahydrofuran, ethylene glycol dimethyl ether or ethylene glycol diethyl ether, ketones such as acetone or butanone, nitriles such as acetonitrile or propionitrile; amides such as dimethylformamide, dimethylacetamide, N-methylformanilide, N-methylpyrrolidone or hexamethylphosphoric triamide, esters such as ethyl acetate, sulfoxides such as dimethyl sulfoxide or acids such as, for example, acetic acid.

If appropriate, process (a) according to the invention can be carried out in the presence of a reaction auxilary. Suitable reaction auxiliaries are all customary inorganic or organic bases. These include, for example, alkali metal hydroxides, such as sodium hydroxide or potassium hydroxide, alkali metal carbonates such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out process (a) according to the invention, the reaction temperatures can be varied within a substantial range. In general, the process is carried out at temperatures between −20° C. and +120° C., preferably at temperatures between 0° C. and +50° C.

To carry out process (b) according to the invention, 1.0 to 2.5 mol, preferably 1.0 to 1.5 mol, of sulfenyl halide of the formula (III) and, if appropriate, 1.0 to 2.5 mol, preferably 1.0 to 1.5 mol, of reaction auxiliary are generally employed per mol of pyridylpyrazole of the formula (II). The reaction is carried out and the reaction products of the formula (Ia) are worked up and isolated by generally customary processes.

Suitable diluents for carrying out process (b) according to the invention are also inert organic solvents. The following are preferably used: hydrocarbons such as benzine, benzene, toluene, hexane or petroleum ether; chlorinated hydrocarbons such as dichloromethane, 1,2-dichloroethane, chloroform, carbon tetrachloride or chlorobenzene; ethers such as diethyl ether, dioxane or tetrahydrofuran; carboxylic acids such as acetic acid or propionic acid, or dipolar aprotic solvents such as acetonitrile, acetone, ethyl acetate or dimethylformamide.

If appropriate, process (b) according to the invention can be carried out in the presence of an acid-binding agent. Suitable acid-binding agents are all organic and inorganic acid-binding agents which can customarily be used. Substances which are preferably used are the hydroxides, acetates or carbonates of alkaline earth metals or alkali metals, such as, for example, calcium hydroxide, sodium hydroxide, sodium acetate or sodium carbonate.

If appropriate, process (b) according to the invention can be carried out in the presence of a suitable catalyst. Suitable catalysts are all metal salt catalysts which are conventionally used for such sulfur oxidation processes. Ammonium molybdate and sodium tungstate may be mentioned in this context by way of example.

When carrying out process (b) according to the invention, the reaction temperatures can be varied within a substantial range. In general, the process is carried out at temperatures between −20° C. and +70° C., preferably at temperatures between 0° C. and +50° C.

To carry out process (b) according to the invention, 0.8 to 1.2 mol, preferably equimolar amounts, of oxidant are generally employed per mol of pyridylpyrazole of the formula (Ia) if it is desired to interrupt the oxidation of the sulfur at the sulfoxide level. To oxidize the compound to the sulfone, 1.8 to 3.0 mol, preferably twice the molar amounts, of oxidant are generally employed per mol of substituted pyridylpyrazole of the formula (Ia). The reaction is carried out and the end products of the formula (Ib) are worked up and isolated by customary processes.

Suitable oxidants for carrying out process (b) according to the invention are all oxidants which can conventionally be used for the oxidation of sulfur. Particularly suitable substances are hydrogen peroxide, organic peracids such as, for example, peracetic acid, m-chloroperbenzoic acid or p-nitroperbenzoic acid, or atmospheric oxygen.

The active compounds are suitable for combating animal pests, preferably arthropods and nematodes, in particular insects and arachnids, encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella inmaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix, Pediculus humanus corporis,* Haematopinus spp., Linognathus spp., Phthirus spp. and Solenopotes spp.

From the order of the Mallophaga, for example, Trichodectes spp., Damalinea spp., Baricola spp., Felicola spp. and Columbicula spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Macrosiphum avenae,* Myzus spp., Pemphigus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae, Tipula paludosa,* Haematobia spp., Chrysops spp., Hydrotaca spp., Phlebotomus spp. and Latromyia spp.

From the order of the Siphonaptera, for example, *Xenopsylla cheopis,* Ceratophyllus spp., Polex spp., Ctenocephalides spp. and Echichrophaga spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds according to the invention is not only active against plant, hygiene and stored product pests, but also, in the veterinary medicine sector, against animal parasites (ectoparasites and endoparasites), such as scaly ticks, argasidae, scab mites, trombidae, flies (stinging and sucking), parasitic fly larvae, lice, hair lice, bird lice, fleas and endoporasitic worms.

They are active against normally sensitive and resistant species and strains, as well as against all parasitic and non-parasitic stages of development of the ecto- and endoparasites.

The active compounds according to the invention are distinguished by a strong insecticidal and acaricidal activity.

They can be employed particularly successfully for combating pests which are parasites of warm-blooded species such as, for example, against the larvae of the green bottle fly (*Lucilia cuprina*), against cattle ticks (*Boophilus microplus*), against scab mites (*Psoroptes ovis*), against cockroaches (*Blattella germanica* and the like), against flies (*Musca domestics*) and against fleas (*Ctenophalides felis*).

Furthermore, the compounds according to the invention show an activity against parasitic protozoans, in particular against Coccidium species, Plasmodium, and against insects and mites which are harmful to plants.

While having low toxicity to warm-blooded species, the active compounds are suitable for combating animal pests, such as arthropods, preferably insects and arachnids, encountered in animal keeping and livestock breeding in domestic animals and productive livestock, and also zoo animals, laboratory animals, experimental animals and pets. In this context, they are active against all or individual stages of development of the pests and against resistant and normally-sensitive species.

By combating the animal pests, it is intended to reduce diseases and their transmission, deaths and reduced peformance (for example in the production of meat, milk, wool, hides, eggs), so that more economical and simpler animal keeping is possible, or only made possible in certain sectors by using the active compounds.

The pests include:

from the order of the Anoplura, for example, Haematopinus spp., Linognathus spp., Solenopotes spp., Pediculus spp., Pthirus spp.;

from the order of the Mallophaga, for example, Trimenopon spp., Menopon spp., Eomenacanthus spp., Menacanthus spp., Trichodectes spp., Felicola spp., Damalinea spp., Bovicola spp.;

from the order of the Diptera, for example, Chrysops spp., Tabanus spp., Musca spp., Hydrotaea spp., Muscina spp., Haematobasca spp., Haematobia spp., Stomoxys spp., Fannia spp., Glossina spp., Luculia spp., Calliphora spp., Auchmeromyia spp., Cordylobia spp., Cochliomyia spp., Chrysomyia spp., Sarcophaga spp., Wohlfartia spp., Gasterophilus spp., Oesteromyia spp., Oedemagena spp., Hypoderma spp., Oestrus spp., Rhinoestrus spp., Melophagus spp., Hippobosca spp.

From the order of the Siphonaptera, for example, Ctenocephalides spp., Echidnophaga spp., Ceratophyllus spp.

From the order of the Metastigmata, for example, Hyalomma spp., Rhipicephalus spp., Boophilus spp., Amblyomma spp., Haemophysalis spp., Dermacentor spp., Ixodes spp., Argas spp., Ornithodorus spp., Otobius spp.;

from the order of the Mesastigmata, for example, Dermanyssus spp., Ornithonyssus spp., Pneumonyssus spp.

From the order of the Prostigmata, for example, Cheyletiella spp., Psorergates spp., Myobia spp., Demodex spp., Neotrombicula spp.;

from the order of the Astigmata, for example, Acarus spp., Myocoptes spp., Psoroptes spp., Chorioptes spp., Otadectes spp., Sarcoptes spp., Notoedres spp., Knemidocoptes spp., Necknemidocoptes spp., Lytodites spp., Laminosioptes spp.

The domestic animals and productive livestock include mammals such as, for example, cattle, sheep, goats, horses, pigs, dogs, cats, camels, water buffalo, donkeys, rabbits, fallow deer, reindeer, fur-bearing animals such as, for example, mink, chinchilla, racoon, birds such as, for example, chickens, turkeys, pheasants, geese, ducks.

Laboratory animals and experimental animals include, for example, mice, rats, guinea pigs, golden hamsters, dogs and cats.

Pets include, for example, dogs and cats.

Administration can be effected prophylactically as well as therapeutically.

The active compounds are administered, directly or in the form of suitable preparations, enterally, parenterally, dermally, nasally, by environment treatment, or with the aid of active-compound-containing shaped articles such as, for example, strips, plates, bands, collars, ear marks, limb bands, marking devices.

The active compounds are administered enterally, for example orally, in the form of powders, tablets, capsules, pastes, boli, potions, granules, or solutions, suspensions and emulsions which can be administered orally, medicated feed or drinking water. Dermal administration is effected, for example, in the form of dipping, spraying or pouring-on and spotting-on and dusting. Parenteral administration is effected, for example, in the form of an injection (intramuscular, subcutaneous, intravenous) or by implants.

Particular mention may be made of the preparations for dermal administration. These include solutions, suspension concentrates and emulsion concentrates, as well as microemulsions which are diluted with water before use, pour-on and spot-on formulations, powders and dusts, aerosols and active-compound-containing shaped articles, as well as dust bags and back rubbers.

The surface-active substances include:

emulsifiers and wetting agents such as anionic surfactants, for example alkylsulfonates, alkyl sulfates, arylsulfonates, sodium lauryl sulfates, fatty alcohol ether sulfates, the monoethanolamine salt of mono/dialkyl polyglycol ether orthophosphoric ester, and calcium alkylarylsulfonate;

cationic surfactants, for example cetyltrimethylammonium chloride;

ampholytic surfactants, for example disodium N-lauryl-beta-iminodipropionate or lecithin;

non-ionic surfactants, for example polyoxyethylated castor oil, polyoxyethylated sorbitan monooleate, polyoxyethylated sorbitan monostearate, glycerol monostearate, polyoxyethylene stearate, alkylphenol polyglycol ethers, polyoxyethylated sorbitan monopalmitate, polyoxyethylene lauryl ether, polyoxyethylene oleyl ether, polyoxyethylene mannitan monolaurate, alkyl polyglycol ethers, oleyl polyglycol ethers, dodecyl polyglycol ethers, ethoxylated nonylphenol, isooctylphenolpolyethoxyethanol.

The preparations may furthermore comprise:

tackifiers, for example carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, paraffins, oils, waxes, hydrogenated castor oil, lecithins and synthetic phospholipids.

The preparations may comprise colorants such as inorganic pigments, for example iron oxide, titanium oxide, Prussion Blue, and organic dyestuffs, such as alizarin, azo and metal phthalocyanine dyestuffs.

The preparations may comprise spreading agents, for example silicone oils of various degrees of viscosity, fatty acid esters such as ethyl stearate, di-n-butyl adipate, hexyl laurate, dipropylene-glycol pelargonate, esters of a branched fatty acid of medium chain length with saturated fatty alcohols $C_{16}$–$C_{18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters, dibutylphthalate, diisopropyl adipate, ester mixtures related to the latter and the like;

triglycerides such as caprylic/capric acid triglyceride, triglyceride mixtures with vegetable fatty acids of chain length $C_8$–$C_{12}$ or other specifically selected natural fatty acids, partial glyceride mixtures of saturated or unsaturated, optionally hydroxyl-containing fatty acids, mono/diglycerides of the $C_8/C_{10}$-fatty acids, and others;

fatty alcohols, such as isotridecyl alcohol, 2-octyldodecanol, cetylstearyl alcohol, oleyl alcohol.

To prepare solid preparations, the active compound is mixed with suitable carriers, if appropriate with the addition of adjuvants, and the mixture is formulated as desired.

Carriers which may be mentioned are all physiologically acceptable solid inert substances. Suitable as such are inorganic and organic substances. Examples of inorganic substances are optionally crushed and fractionated, for example synthetic and natural ground minerals, such as kaolins, talc, chalk, quartz, diatomaceous earth, sodium chloride, carbonates such as calcium carbonate, hydrogen carbonates, aluminum oxides, silicas, clays, precipitated or colloidal silicon dioxide, and phosphates.

Examples of organic substances are sugars, cellulose, foods and animal feeds such as dried milk, carcass meals, cereal meals and coarse cereal meals, starches and sawdust.

Adjuvants are preservatives, antioxidants and colorants which have already been indicated further above.

Other suitable adjuvants are lubricants and glidants agents such as, for example, magnesium stearate, stearic acid, talc, bentonites, disintegrants such as starch or crosslinked polyvinylpyrrolidone, binders such as, for example, starch, gelatine or linear polyvinylpyrrolidone, and also dry binders such as microcrystalline cellulose.

In the form of their abovementioned solid or liquid formulations, the active compounds can also be encapsulated.

The active compounds can also be applied in the form of an aerosol. To this end, the active compound, which is suitably formulated, is finely distributed using pressure.

It may also be advantageous to use the active compounds in formulations which release the active compound in a delayed fashion. Such formulations which may be mentioned are active-compound-containing shaped articles such as, for example, plates, bands, strips, collars, ear tags, tail tags, limb bands, halters and marking devices. Other such formulations which may be mentioned are active-compound-containing implants and boli.

The active compounds can also be administered together with the feed and/or the drinking water.

The active compounds can be present in the formulations on their own or in the form of a mixture with other active compounds or synergists.

Formulations which are administered directly comprise between $10^{-7}$ and 5% by weight, preferably between $10^{-4}$ and 1% by weight, of active compound.

Formulations which are only used after further dilution comprise 1 to 95% by weight, preferably 5 to 90% by weight, of active compound.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example ligninsulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The following compounds may be mentioned:

acrinathrin, alphamethrin, betacyfluthrin, bifenthrin, brofenprox, cis-resmethrin, clocythrin, cycloprothrin, cyfluthrin, cyhalothrin, cypermethrin, deltamethrin, esfenvalerate, etofenprox, fenpropathrin, fenvalerate, flucythrinate, fluvalinate, lambda-cyhalothrin, permethrin, pyresmethrin, pyrethrum, silafluofen, tralomethrin, zetamethrin, alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chlorpyrifos M, cyanophos, demeton M, demeton-S-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion, phorate, malathion, mecarbam, mevinphos, mesulfenphos, methacrifos, methamidophos, naled, omethoate, oxydemeton M, oxydeprofos, parathion A, parathion M, phenthoate, phorate, phosalone, phosmet, phosphamidon, phoxim, pirimiphos A, pirimiphos M, propaphos, prothiophos, prothoate, pyraclophos, pyridaphenthion, quinalphos, salithion, sebufos, sulfotep, sulprofos, tetrachlorvinphos, temephos, thiomethon, thionazin, trichlorfon, triazophos, vamidothion, buprofezin, chlorfluazuron, diflubenzuron, flucycloxuron, flufenoxuron, hexaflumuron, pyriproxifen, tebufenozide, teflubenzuron, triflumuron, imidacloprid, nitenpyram, N-[(6-chloro-3-pyridinyl)-methyl]-N'-cyano-N-methylethaneimideamide(NI-25), abamectin, amitrazin, avermectin, azadirachtin, bensultap, Bacillus thuringiensis, cyromazine, diafenthiuron, emamectin, ethofenprox, fenpyrad, fipronil, flufenprox, lufenuron, metaldehyd, milbemectin, pymetrozine, tebufenpyrad, triazuron, aldicarb, bendiocarb, benfuracarb, carbofuran, carbosulfan, chlorethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, silafluofen, tebupirimphos, tefluthrin, terbufos, thiodicarb, thiafenox, azocyclotin, butylpyridaben, clofentezine, cyhexatin, diafenthiuron, diethion, emamectin, fenazaquin, fenbutatin oxide, fenothiocarb, fenpropathrin, fenpyrad, fenpyroximate, fluazinam, fluazuron, flucycloxuron, flufenoxuron, fluvalinate, fubfenprox, hexythiazox, ivemectin, methidathion, monocrotophos, moxidectin, naled, phosalone, profenofos, pyraclofos, pyridaben, pyrimidifen, tebufenpyrad, thuringiensin, triarathene as well as 4-bromo-2-(4-chlorophenyl)-1-(ethoxymethyl-5-(trifluoromethyl)-1H-pyrrole-3-carbonitrile (AC 303630).

The active compound according to the invention can furthermore be present in its commercially available formulations and in the use forms prepared from these formulations as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The application of the active compound takes place in a customary manner appropriate for the use forms.

When used against hygiene pests and pests of stored products, the active compound is distinguished by an excellent residual action on wood and clay as well as a good stability to alkali on limed substrates.

The active compound according to the invention is also suitable for combating insects, mites, ticks etc. in the sectors of animal keeping and livestock breeding; better results, for example higher milk production, greater weight, more attractive animal pelt, longer life etc., can be achieved by combating the pests.

The application of the active compound according to the invention occurs in this sector in a known fashion, such as by external application in the form of, for example, dipping, spraying, pouring-on and spotting-on and dusting, as well as by means of parenteral application in the form, for example, of an injection, and, furthermore, by means of the feed-through process. In addition, application as shaped articles (collar, ear tag) or in the form of a so-called environment treatment is also possible. The preparation and biological effectiveness of the compound according to the invention will be explained with reference to the examples below.

PREPARATION EXAMPLES

Example 1

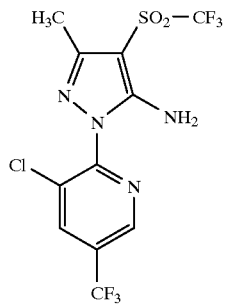

2.4 g (0.006 mol) of 5-amino-3-methyl-4-trifluoromethylthio-[(3-chloro-5-trifluoromethyl)-2-pyridyl]-pyrazole (Ex. 2) are dissolved in 30 ml of acetic acid, and a spatula-tipful of sodium tungstate is added. 10 g (0.086 mol) of 30% strength hydrogen peroxide solution are added dropwise to this solution at room temperature. Stirring is then continued for 18 hours. The reaction mixture is then diluted with approximately 100 ml of water. The precipitate is filtered off and dried.

1.4 g (54% of theory) of 5-amino-3-methyl-4-trifluoromethylsulfonyl-[(3-chloro-5-trifluoromethyl)-2-pyridyl]-pyrazole are obtained as a pale yellow solid of melting point 93° C.

Example 2

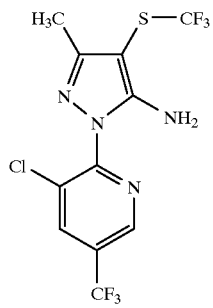

6.6 g (0.024 mol) of 5-amino-3-methyl-[(3-chloro-5-trifluoromethyl)-2-pyridyl]-pyrazole are dissolved in 60 ml of absolute dichloromethane, and 2.1 g (0.026 mol) of absolute pyridine are added. The mixture is then cooled to 0–5° C., and 3.6 g (0.026 mol) of trifluoromethylsulfenyl chloride are added dropwise. The mixture is stirred for 3 hours at 0° C. and then overnight at room temperature. The mixture is subsequently washed twice using water and dried using magnesium sulfate, and the solvent is stripped off in vacuum.

6 g (67% of theory) of 5-amino-3-methyl-4-trifluoromethylthio-[(3-chloro-5-trifluoromethyl)-2-pyridyl]-pyrazole are obtained as a reddish brown wax.

Preparation of the Starting Material

Example (II)

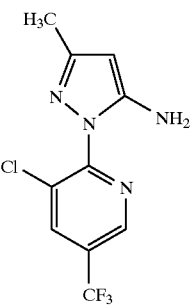

12 g (0.057 mol) of 3-chloro-5-(trifluoromethyl)-pyrid-2-ylhydrazine and 4.7 g (0.057 mol) of 3-aminocrotonitrile are refluxed for 24 hours in 100 ml of ethanol and 1 ml of concentrated sulfuric acid. Then, a further 4 ml of concentrated sulfuric acid are added, and stirring is continued for 8 hours at 60° C. The solvent is subsequently removed by filtration with suction in vacuo, and the orange residue is taken up in water and dichloromethane. The dichloromethane phase is separated off and dried over magnesium sulfate, and the solvent is removed in vacuo.

7.8 g (49% of theory) of 5-amino-3-methyl-[(3-chloro-5-trifluoromethyl)-2-pyridyl]-pyrazole are obtained as a viscous reddish brown oil.

Example 3

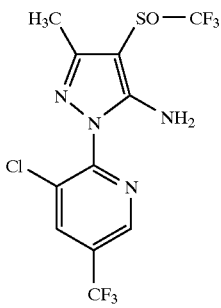

9 g (0.024 mol) of 5-amino-3-methyl-4-trifluoromethylthio-[(3-chloro-5-trifluoromethyl)-2-pyridyl]-pyrazole (Ex. 2) are dissolved in 50 ml of dichloromethane, and 8.5 g (0.027 mol) of 55% strength m-chloroperbenzoic acid are added in portions. The mixture is stirred for a further 48 hours at room temperature. Then, the precipitate is filtered off and discarded. The filtrate is washed using sodium carbonate solution and subsequently using dilute sodium hydroxide solution. The organic phase is dried over magnesium sulfate and then concentrated in vacuo. 6.2 g of red resin remain as residue, and this is chromatographed over approximately 400 g of silica gel 60. Using cyclohexane/ethyl acetate (2:1) as the eluent, 1.9 g (20% of theory) of 5-amino-3-methyl-4-trifluoromethylsulfinyl-[(3-chloro-5-trifluoromethyl)-2-pyridyl]-pyrazole are obtained as a viscous orange oil.

$^1$H NMR data*): 9.0 ppm (d, 1H); 8.82 ppm (d, 1H); 6.9 ppm (bs, NH$_2$); 2.2 ppm (s, 3H).

*)The $^1$H NMR spectra were recorded in deuterochloroform (CDCl$_3$) or hexadeuterodimethyl sulfoxide (DMSO-d$_6$) using tetramethylsilane (TMS) as the internal standard. The data given are the chemical shift as δ value in ppm.

Use Examples

In the Use Examples which follow, the compound given below is used as comparison substance:

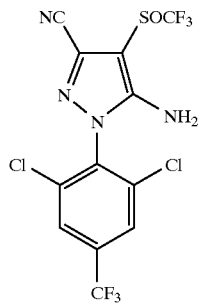
(A)

5-amino-3-cyano-4-trifluoromethyl-sulfinyl-1-[2,6-dichloro-4-(trifluoromethyl)-phenyl]-pyrazole (disclosed in EP-A 295 117)

Example A

Test for Residual Action

To test the efficacy of active compounds, a variety of substrates such as, for example, PVC floor coverings, unglazed tiles, fired clay, clay+Ca(OH)$_2$ and plywood were sprayed with preparations, formulated as wettable powders (WP), in the form of aqueous suspensions using certain application rates (mg of a.i./m$^2$).

Every week, starting one week after the treatment up to 4 weeks, 10 cockroaches of the species *Blattella germanica* in the 5th larval stage and 20 female house flies of the species *Musca domestica* were placed on the substrate in question. The cockroaches were kept on the treated areas inside talcum-treated glass rings, flies by means of wire mesh cages, and the animals remained on the substrate for 24 hours.

The percentage destruction was determined 15 and 30 minutes as well as hourly one to 6 hours after the experiment had been set up. Further evaluations were made after 8 and 24 hours.

In this example, for example compound (1) according to the invention in the form of a 10% wettable powder applied at 1000 mg a.i./m$^2$ shows a considerably better residual action on a variety of surfaces such as, for example, PVC, wood, unglazed tile, clay, and clay and chalk, than compound (A), which is known from the prior art.

Example B

Blowfly Larvae Test

Test subject: *Lucilia cuprina* larvae

Emulsifier: 35 parts by weight of ethylene glycol monomethyl ether 35 parts by weight of nonylphenol polyglycol ether To produce a suitable preparation of active compound, 3 parts by weight of active compound are mixed with 7 parts by weight of the abovementioned mixture, and the resulting emulsion concentrate is diluted with water to the desired concentration.

Approximately 20 *Lucilia cuprina* larvae (which are resistant to a multiplicity of active compounds) are introduced into a test tube containing approximately 1 cm$^3$ of horse meat and 0.5 ml of the preparation of active compound. After 24 to 48 hours, the efficacy of the preparation of active compound is determined. 100% means that all blowfly larvae have been killed; 0% means that no blowfly larvae have been killed.

In this test, a 100% activity against *Lucilia cuprina* is shown by compounds 1 and 2 according to the invention when used at an active compound concentration of 100 ppm, while the prior art is ineffective (0%).

Example C
In-vivo Tick Test/Spray Treatment of Cattle
Test subject: All stages of *Boophilus microplus* (larvae, metalarvae, nymphs, metanymphs, adults), pyrethroid-resistant strain
Emulsifier: 35 parts by weight of ethylene glycol monomethyl ether
35 parts by weight of nonylphenol polyglycol ether
To produce a suitable preparation of active compound, 3 parts by weight of active compound are mixed with 7 parts by weight of the abovementioned mixture, and the resulting emulsion concentrate is diluted with water to the desired concentration.

Cattle are infected 14 times at 2 day intervals with approximately 3000 fasting, 14–28-day-old *Boophilus microplus* larvae. On day 23 after the infection, the beast is sprayed uniformly with 5 liters of the abovementioned preparation of active compound (hand-held sprayer, 6 atmospheres above atmospheric atmosphere). From day 24 to day 45 after the infection, the developing female adults are counted and the fertility of the egg clusters of these ticks is checked, and these data are used for determining the efficacy of the preparation of active compound. 100% means that no ticks with fertile egg clusters have been found; 0% means that the number of ticks and the fertility of the egg clusters were similar to the control.

In this test, compound 1 shows an activity of 100% against *Boophilus microplus* when used at active compound concentrations of 30 ppm and 100 ppm, while the prior art (A) only results in an activity of 83% when used at 100 ppm.

It will be understood-that the specification and examples are illustrative but not limitative of the present invention and that other embodiments within the spirit and scope of the invention will suggest themselves to those skilled in the art.

What is claimed is:

1. A substituted pyridylpyrazole of the formula.

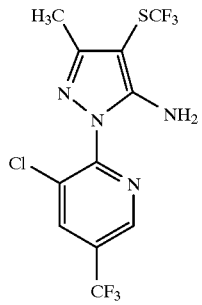

2. A substituted pyridylpyrazole of the formula.

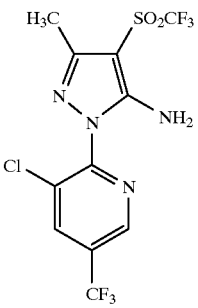

3. A pesticidal composition comprising a pesticidally effective amount of a compound of the formula

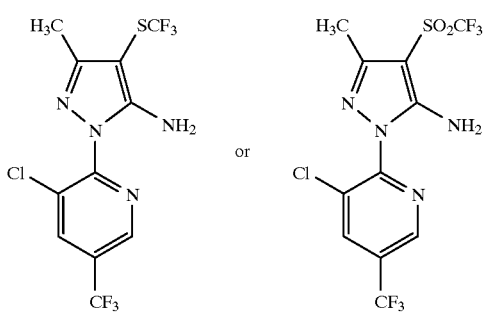

and a diluent.

4. A method of combatting moths on larvae of nephotettix which comprises applying to said moths or larvae or to a locus from which it is to be excluded an insecticidally effective amount of a compound of the formula.

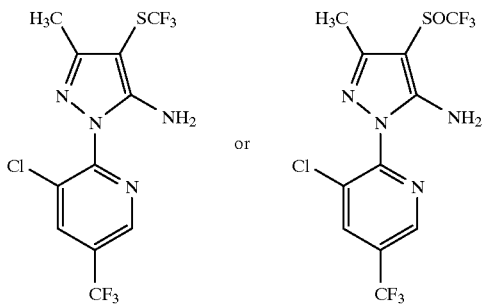

5. The method according to claim 4 wherein the locus is vegetation.

* * * * *